United States Patent [19]
Keil et al.

[11] Patent Number: 5,801,296
[45] Date of Patent: Sep. 1, 1998

[54] PROCESS FOR AUTOMATED MEASUREMENT OF AMMONIA CONTENT IN A GAS MIXTURE

[75] Inventors: Gary D. Keil, Elmwood; Ronald G. Morgan; Sheryl A. Tipton, both of East Peoria; Wayne A. Supak, Washington, all of Ill.

[73] Assignee: Caterpillar Inc., Peoria, Ill.

[21] Appl. No.: 900,684

[22] Filed: Jul. 25, 1997

Related U.S. Application Data

[62] Division of Ser. No. 799,754, Feb. 11, 1997.

[51] Int. Cl.$^6$ ............... G01N 33/18; G01N 7/00
[52] U.S. Cl. ............... 73/19.1; 73/31.04; 73/31.07
[58] Field of Search ............... 73/19.1, 23.2, 73/31.04, 31.07, 31.03; 423/351; 95/232; 422/83; 55/95, 96; 436/113, 178

[56] References Cited

U.S. PATENT DOCUMENTS

| | | |
|---|---|---|
| 5,141,873 | 8/1992 | Steudel et al. ............... 436/148 |
| 5,211,055 | 5/1993 | Steudel et al. ............... 74/64.47 |
| 5,222,032 | 6/1993 | Fleming ............... 364/502 |

Primary Examiner—Hezron E. Williams
Assistant Examiner—Jay L. Politzer
Attorney, Agent, or Firm—Kevin M. Kercher

[57] ABSTRACT

A process for automated measurement of ammonia in a gas mixture containing ammonia gas and one or more water-insoluble gases includes providing a water reservoir adapted for supplying water therefrom through a first solenoid valve and providing a measurement vessel adapted for receiving water. The vessel is adapted for draining the water therefrom through a second solenoid valve. The vessel is also adapted for receiving the gas mixture through a third solenoid valve and purging the gas mixture from the vessel through a fourth solenoid valve. The vessel is adapted for maintaining the gas in the vessel and receiving water thereinto in an amount sufficient to dissolve the ammonia gas contained in the gas mixture, into the water, and allowing a differential pressure between the gas mixture and the water containing dissolved ammonia to be measured. The process also includes providing a measurement vessel adapted for allowing height of water within the vessel to be measured, providing means for measuring height of water within measurement vessel, and providing recording means for converting the measured height signal to an ammonia concentration value.

17 Claims, 3 Drawing Sheets

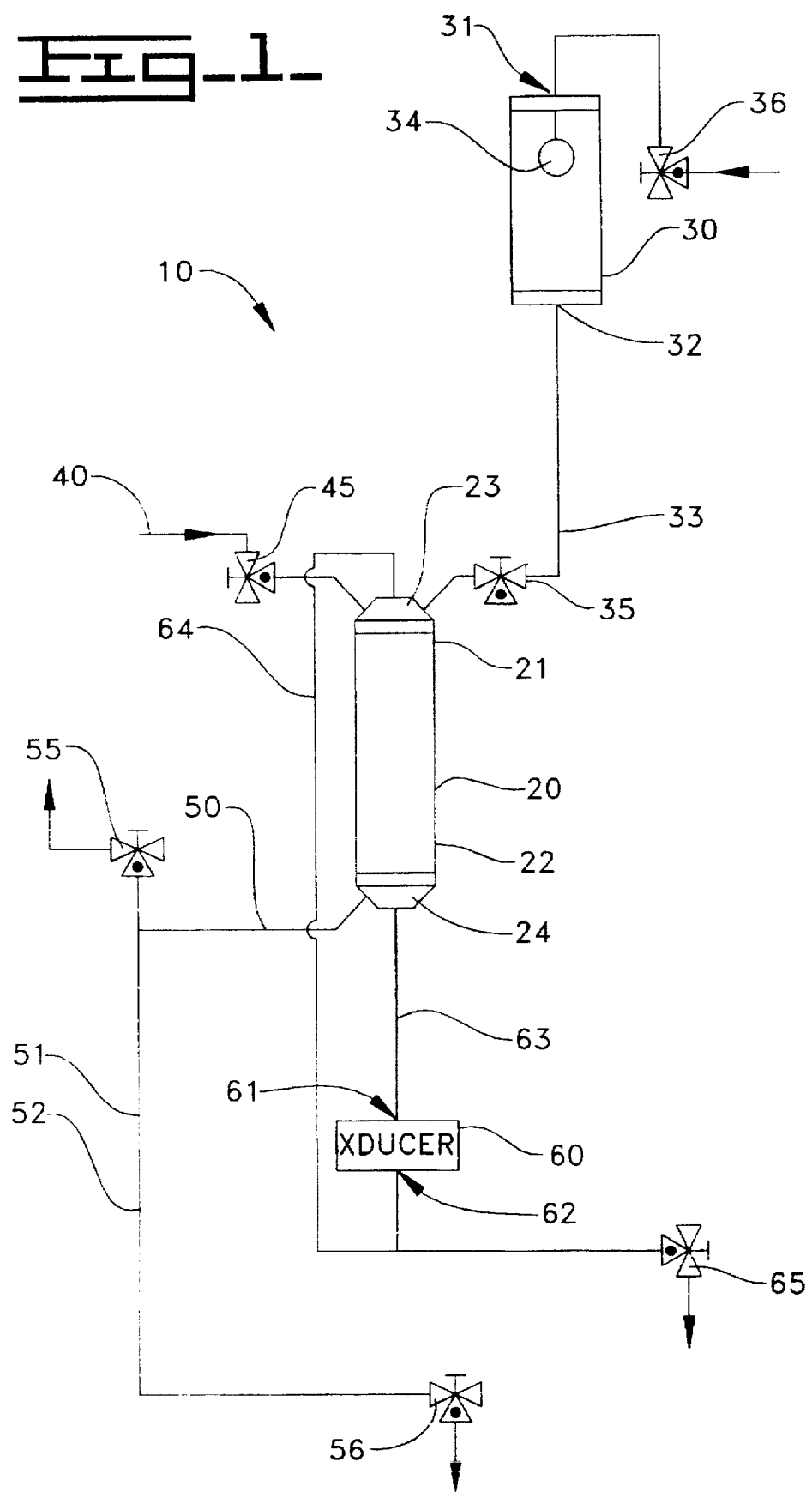
Fig_1_

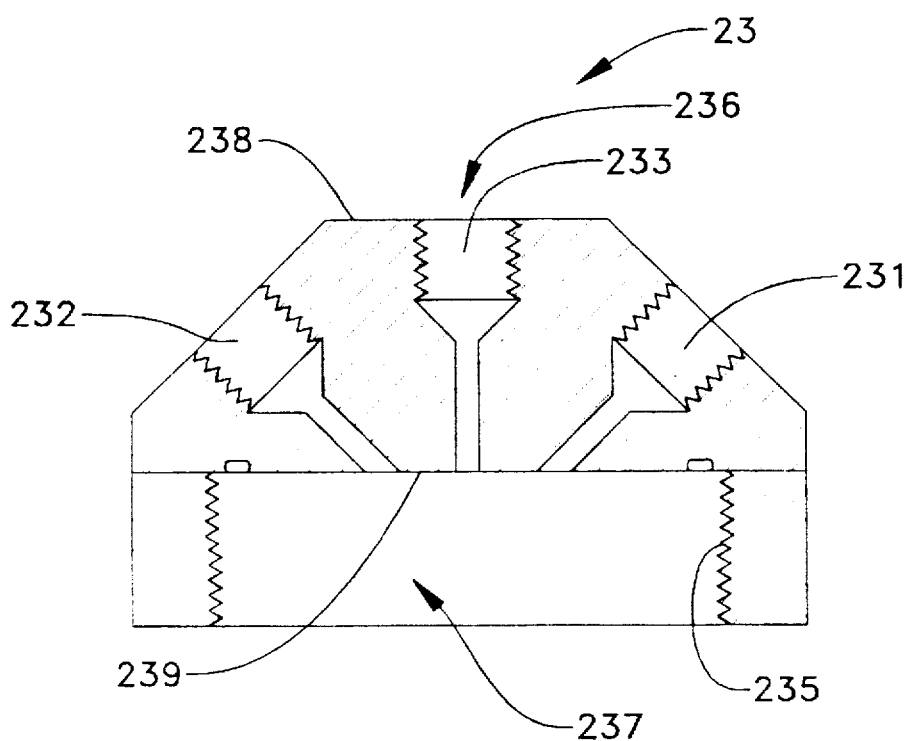
Fig_2_
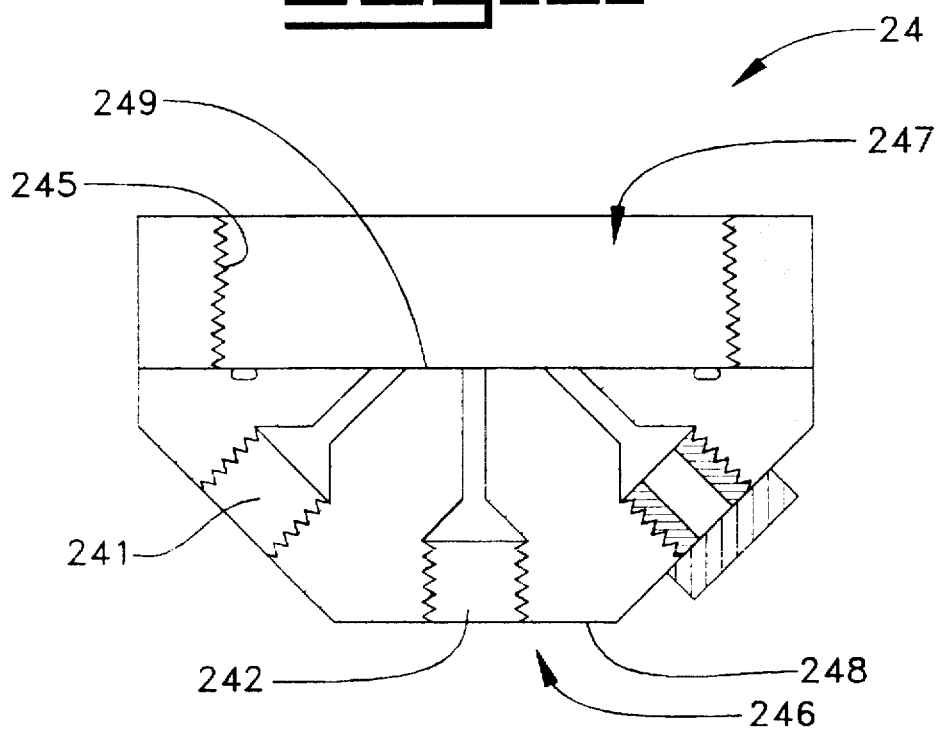
Fig_3_

Fig_4_
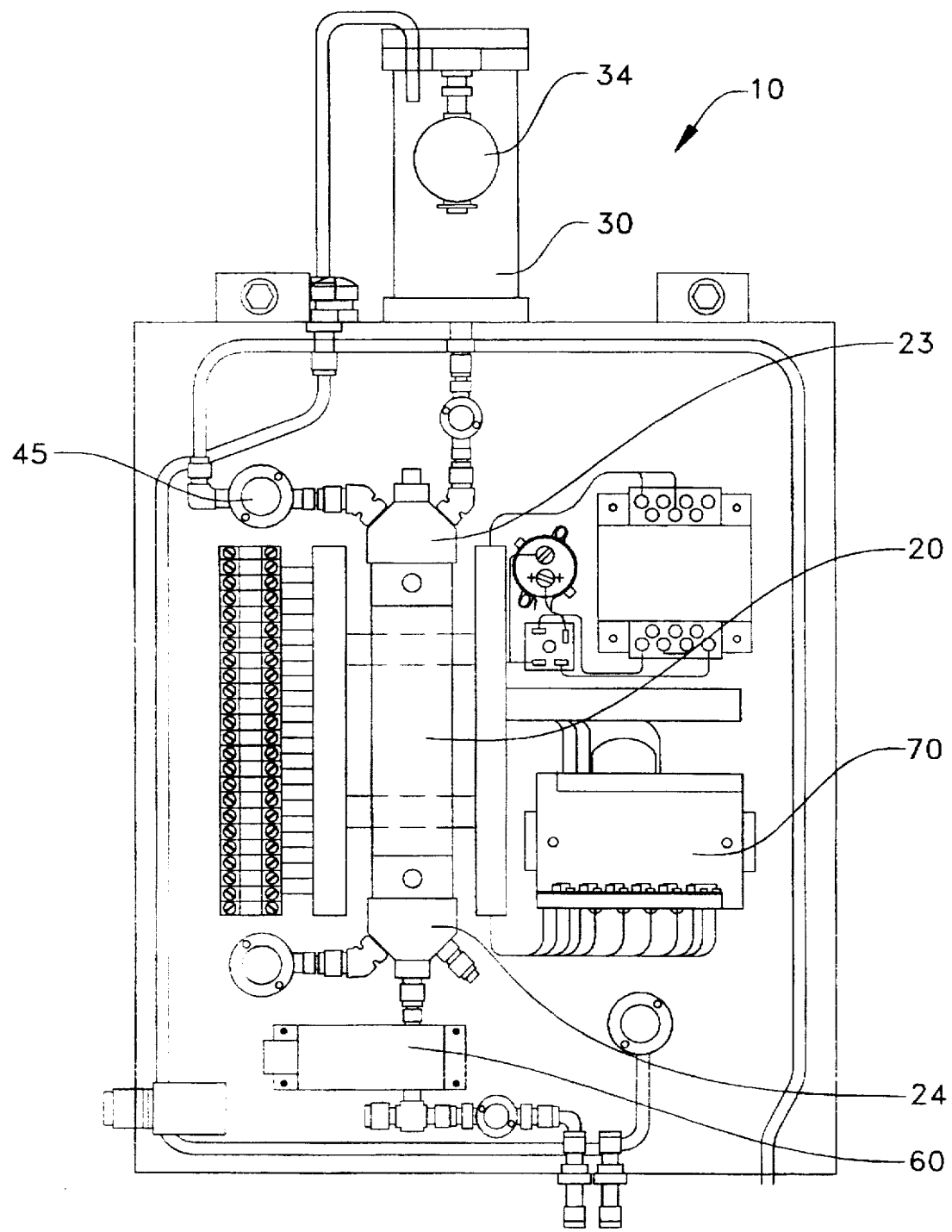

5,801,296

1

PROCESS FOR AUTOMATED MEASUREMENT OF AMMONIA CONTENT IN A GAS MIXTURE

This is a divisional application of application Ser. No. 08/799,754, filed Feb. 11, 1997.

TECHNICAL FIELD

The present invention relates generally to measurement of ammonia concentration in gases, and particularly, to an apparatus and method for automated measurement of ammonia gas in a gas mixture wherein all of the other gases present in the gas mixture, with the exception of ammonia, are insoluble in water.

BACKGROUND ART

In operations involving the heat treatment of steel parts in a furnace, the measurement and control of the furnace atmosphere gas concentration is necessary to obtain optimal properties of the heat treated parts. The ammonia concentration in the furnace atmosphere gas plays a critical role in controlling nitriding operations.

Various methods are known for measuring the ammonia concentration in a gas mixture. Methods in which the ammonia concentration is determined directly in the gaseous phase are usually based on the photometry of the ammonia in the infrared range. In these methods, the intensity of infrared light absorbed in, transmitted by, or reflected from a gas sample is quantitatively measured and compared against a reference light intensity, thereby providing a quantitative measurement of ammonia concentration in the gas sample. Such methods, although accurate, are not robust enough for survival in a production environment involving heat treatment operations. Furthermore, in infrared methods, the accuracy of ammonia concentration measurement is jeopardized due to the interference of other gases and it has been found that the infrared analyzer drifts and requires daily calibration to improve accuracy. This daily calibration requires extensive and expensive certified gases. This is a severe disadvantage for using an infrared analyzer in a rigorous production environment.

Another method for determining the ammonia concentration in the gas phase is, based on the combustion of ammonia on a catalyst and then measuring the heat of the reaction. Again, these methods are cumbersome and not robust enough for surviving in a rigorous production environment involving heat treating operations of large steel parts.

Methods in which ammonia in the gas phase is dissolved into a liquid phase, and the concentration of ammonia in solution is then determined, are used more frequently. However, such commercially available methods involve determining ammonia concentration using a glass burette and petcock valves for manually collecting gas samples, exposing the gas sample to water and determining the ammonia concentration by visually measuring water column height in the glass burette. Such methods have the disadvantage of being more time consuming and are prone to operator error and are usually operated in a discontinuous manner.

It has been desirable to have an automated process and apparatus for continuous monitoring of ammonia concentration in furnace atmosphere gases. It has been desirable to have an automated measurement system based on the determination of ammonia concentration in solution, which is rigorous, not prone to operator error, and accurate. It has been desirable that the automated measurement system be a primary measurement system that does not require expensive daily calibration and maintenance. It has also been desirable to have an automated ammonia measurement system that is industrially robust and which allows continuous sampling of ammonia concentration.

The present invention is directed to overcome one or more problems, as set forth above.

DISCLOSURE OF THE INVENTION

In one aspect of the present invention, a process for automated measurement of ammonia content in a gas mixture containing water-soluble ammonia gas and one or more water-insoluble gases, is disclosed.

The process includes providing a water reservoir adapted for (i) receiving water therein while maintaining a predetermined water level in the reservoir, and (ii) supplying water therefrom through a first solenoid valve. The process further includes providing a measurement vessel adapted for (i) receiving the water from the reservoir through the first solenoid valve and draining the water from the vessel through a second solenoid valve, (ii) receiving the gas mixture at a predetermined pressure and temperature through a third solenoid valve and purging the gas mixture from the vessel through a fourth solenoid valve, (iii) maintaining the gas in the vessel and receiving the water in the vessel, the water being of an amount sufficient to dissolve the ammonia gas contained in the gas mixture into the water, and (iv) allowing a differential pressure between the gas mixture and the water containing dissolved ammonia to be measured. The process also includes providing a differential pressure transducer having a high pressure port and a low pressure port. The pressure transducer is adapted for (i) sensing the pressure exerted by the water containing dissolved ammonia, at the high pressure port, (ii) sensing the pressure exerted by the gas mixture at the low pressure port, and (iii) providing a voltage signal in response to a differential pressure between the respective pressures exerted by the water and the gas. The process also includes providing a programmable logic controller (PLC) connected electrically to each of (i) the first, second, third and fourth solenoid valves for sequentially operating the solenoid valves, and (ii) the pressure differential transducer. The process further includes providing recording means connected electrically to the differential pressure transducer for collecting the voltage signal from the transducer and converting the voltage signal to an ammonia concentration value and programming the PLC to sequentially open and close the valves.

In another aspect of the present invention, an apparatus for automated measurement of ammonia content in a gas mixture containing water-soluble ammonia gas and one or more water-insoluble gases, is disclosed. The apparatus includes a measurement vessel having a tubular shape, a first end, a second end, a first end cap and a second end cap attached to the first end and the second end respectively. The first end cap has a water inlet port, a gas inlet port and a gas pressure sensing port. The second end cap has a water-gas outlet port and a water pressure sensing port. The apparatus also includes a water reservoir having a water fill port and a water supply port. The water supply port is in fluid communication with the water inlet port of the first end cap of the measurement vessel through a water supply conduit. The water supply conduit has a water inlet solenoid valve disposed therein. The apparatus further includes a gas supply conduit connected at one end to the gas inlet port of the first end cap of the measurement vessel, and at other end to a gas source for supplying the gas mixture. The gas supply conduit has a gas inlet solenoid valve disposed therein. A water-gas outlet conduit is connected at one end to the water-gas outlet port of the second end cap of the measurement vessel. The water-gas outlet conduit bifurcates into a gas outlet conduit and a water outlet conduit. The gas outlet conduit has a gas outlet solenoid valve disposed therein. The water outlet conduit has a water outlet solenoid valve disposed therein. A differential pressure transducer has a high pressure port and a low pressure port. The high pressure port is in fluid communication with the water pressure sensing port of the second end cap of the measurement vessel through a water pressure sensing conduit. The low pressure port is in fluid communication with the gas pressure sensing port of the first end cap of the measurement vessel through a gas pressure sensing conduit. The transducer is capable of producing a voltage signal in response to a sensed differential pressure between water pressure and gas pressure. The apparatus includes a programmable logic controller (PLC) connected electrically to each of the water inlet, gas inlet, gas outlet, and water outlet solenoid valves for sequentially operating the valves. The PLC is also connected to the differential pressure transducer. The apparatus finally includes recording means connected electrically to the differential pressure transducer for collecting the voltage signal from the transducer and converting the voltage signal to an ammonia concentration value.

In yet another aspect of the present invention, a process for automated measurement of ammonia content includes providing a measurement vessel adapted for allowing height of water within the vessel to be measured and providing means for measuring height of water within measurement vessel.

BRIEF DESCRIPTION OF THE DRAWINGS

FIG. 1 is a schematic diagram showing the operational aspects of the process and apparatus of the present invention;

FIG. 2 is a cross-sectional view of the first end cap of the apparatus;

FIG. 3 is a cross-sectional view of the second end cap of the apparatus; and

FIG. 4 is frontal view of the actual embodiment of the apparatus of the present invention.

BEST MODE FOR CARRYING OUT THE INVENTION

In the preferred embodiment of the present invention, a process for automated measurement of ammonia content in a gas mixture containing water soluble ammonia gas and one or more water insoluble gases includes the following steps:

First, a water reservoir is provided. The water reservoir is adapted for receiving water while maintaining a predetermined water level in the reservoir. The water reservoir is also adapted for supplying water therefrom through a first solenoid valve. Preferably, the water level is maintained by means of a float valve.

Second, a measurement vessel is provided. The measurement vessel is adapted for receiving the water from the reservoir through the first solenoid valve and draining the water from the vessel through a second solenoid valve. The measurement vessel is also adapted for receiving the gas mixture at a predetermined pressure and temperature through a third solenoid valve. The measurement vessel is adapted for purging the gas mixture from the vessel through a fourth solenoid valve when desired. The measurement vessel is also adapted for maintaining a fixed volume of gas within the vessel and then receiving water into the vessel. The water received in the vessel is of an amount sufficient to dissolve the ammonia gas contained in the gas mixture into the water. The measurement vessel is also adapted for allowing a differential pressure exerted by the gas and the water to be measured.

Third, a differential pressure transducer is provided. The differential pressure transducer has a high pressure port and a low pressure port. The pressure transducer is adapted for sensing the pressure exerted by the water which contains the dissolved ammonia at the high pressure port of the pressure transducer. The pressure transducer is also adapting for sensing the pressure exerted by the gas mixture in the vessel at the low pressure port of the pressure transducer. The pressure transducer is adapted for providing a voltage signal in response to a differential pressure between the respective pressures exerted by the water and the gas contained in the measurement vessel.

Fourth, a programmable logic controller (PLC) is provided. The PLC is connected electrically to each of the first, second, third and fourth solenoid valves for sequentially operating the solenoid valves in a predetermined sequence. The predetermined sequence, as set forth below, is explained in further detail. The PLC is also electrically connected to the pressure differential transducer.

Fifth, a recording means is provided. The recording means is connected electrically to the differential pressure transducer and is adapted for collecting the voltage signal from the transducer and converting the voltage signal to an ammonia concentration value.

Sixth, a programming sequence for the PLC is provided. The PLC is programmed to sequentially open and/or close the first, second, third and fourth solenoid valves in the following sequence: (i) open the fourth solenoid valve, (ii) open the first solenoid valve, (iii) close the fourth solenoid valve, (iv) open the second solenoid valve, (v) close the second solenoid valve, (vi) close the first solenoid valve, (vii) open the third solenoid valve, (viii) close the third solenoid valve, (ix) energize the recording means to record measured transducer voltage and convert to an ammonia concentration vale, (x) open the fourth solenoid valve, (xi) open the first solenoid valve, (xii) close the fourth solenoid valve, and (xiii) close the first solenoid valve.

In the preferred embodiment of the process of the present invention, the water, which is allowed to enter the measurement vessel after the measurement vessel has a fixed amount of gas contained therein, is of an amount sufficient to substantially dissolve the ammonia gas into the water. And preferably, the water is often an amount sufficient to dissolve at least 90 mole percent of ammonia gas into the water. This is preferred in order to obtain maximum dissolution of ammonia gas into the water and thereby maintaining a high accuracy of the determined ammonia concentration value in the gas mixture.

In the preferred embodiment, the process further includes the step of providing a fifth solenoid valve for draining any entrained water and preventing the entrained water from entering the low pressure port of the differential pressure transducer. This is done in order to maintain a high accuracy of the measured differential pressure. When this fifth solenoid valve is provided, the process also includes the step of connecting the PLC electrically to the fifth solenoid valve and programming the PLC to sequentially operate the fifth solenoid valve by the steps of first opening the fifth solenoid valve and then closing the fifth solenoid valve. The above two steps occur immediately after the sequential step numbered (xii) in the opening and closing sequence provided above.

In another embodiment of the present invention, an apparatus for automated measurement of ammonia content in a gas mixture containing water soluble ammonia gas and one or more water insoluble gases is provided. Referring now to FIG. 1, the apparatus 10 includes a measurement vessel 20 having a tubular shape, a first end 21, a second end 22, a first end cap 23 and a second end cap 24. The first and second end caps are attached to the first and second ends respectively.

Referring now to FIG. 2, in the preferred embodiment, the first end cap 23 has a water inlet port 231, a gas inlet port 232 and a gas pressure sensing port 233. Referring now to FIG. 3, in the preferred embodiment, the second end cap 24 preferably has a water gas outlet port 241 and a water pressure sensing port 242. For the sake of practicality, the first and second end caps are of identical construction but the second end cap has one of the ports closed by a plug, as shown in FIG. 3.

Referring back to FIG. 1, apparatus 10 also includes a water reservoir 30 having a water fill port 31 and a water supply port 32. The water supply port 32 is in fluid communication with the water inlet port 231 of the first end cap 23 of the measurement vessel 20 through a water supply conduit 33. The water supply conduit has a water inlet solenoid valve 35 disposed therein.

In the preferred embodiment, the measurement vessel 20 is a cylindrical vessel having an internal diameter desirably in the range of an internal diameter in the range of about 25 mm to about 75 mm and a length in the range of about 100 mm to about 450 mm. Preferably, the measurement vessel has an internal diameter in the range of 50 mm and a length of 250 mm.

Referring now to FIGS. 2 and 3, the first and second end caps 23,24 are desirably removably attached to the first and second ends 21,22 respectively of measurement vessel 20. Preferably, the first and second end caps 23,24 each have internal threads 235,245 respectively for threading onto corresponding external threads adjacent the first and second ends 21,22 of measurement vessel 20. In an alternate embodiment, the first and second end caps may be fixedly attached to the measurement vessel by means such as welding and the like.

Referring again to FIG. 2, in the preferred embodiment of the present invention, the first end cap 23 has a tubular shape, a closed end 236 and an open end 237. The closed end 236 has an outer surface 238 and a planer inner surface 239. As shown in FIG. 2, the ports 231,232,233 extend from the outer surface 238 to the planer inner surface 239. It must be understood that although the shape of the first end cap shown in FIG. 2 is the preferred embodiment, other embodiments are envisioned in and encompassed within this invention and the first end cap may have a hemispherical or a cylindrical outer surface without departing from the present invention. In the preferred embodiment, the gas pressure sensing port 233 is oriented perpendicularly to the planer inner surface 239 and preferably both ports 231 and 232 are oriented at an angle in the range of about 30° to 60° with respect to the port 233. Preferably, the ports 231 and 232 are oriented at an angle of about 45° with respect to port 233 respectively. It was found that unless the angles of the inlet ports were maintained in the desired range as set forth above, the water entering the vessel would mix with the gas and get entrained into the gas pressure sensing port 233, which is undesirable because it creates an error in the sensed differential pressure.

Referring now to FIG. 3, in the preferred embodiment, the second end cap also has a tubular shape, a closed end 246 and an open end 247. Closed end 246 has an outer surface 248 and a planer inner surface 249. The ports 241 and 242 extend from the outer surface 248 to the planer inner surface 249 of the closed end 246. Although in FIG. 3, port 241 is shown as being oriented at an angle with respect to port 242 which is shown as being perpendicularly oriented to surface 249. This is done for the sake of manufacturability. Alternate embodiments wherein ports 241 and 242 are oriented at different angles, or even parallel to each other, are encompassed within this invention. Likewise, the second end cap may have a different outer shape, such as hemispherical, for example.

Referring back to FIG. 1, water reservoir 30 has means for maintaining a water level therein. The means desirably include a float valve 34. Further, the water reservoir 30 is positioned above the measurement vessel 20 to allow gravity feed of the water into the measurement vessel through conduit 33. The water reservoir desirably has an internal volume in the range of about one-and-a-half to ten times the internal volume of the measurement vessel and preferably about six times the internal volume of the measurement vessel. In the preferred embodiment, the water is filled in the water reservoir through a water fill solenoid valve 36.

In the preferred embodiment, the apparatus 10 also includes a gas supply conduit 40 connected at one end to the gas inlet port 232 of first end cap 23. At the other end, the gas supply conduit 40 is connected to a gas source which supplies the gas mixture whose ammonia content is to be measured. The gas supply conduit 40 has a gas inlet solenoid valve 45 disposed therein.

In the preferred embodiment, apparatus 10 also includes a water-gas outlet conduit 50 connected at one to the water-gas outlet port 241 of second end cap 24 of the measurement vessel 20. The water-gas outlet conduit 50 bifurcates into a gas outlet conduit 51 and a water outlet conduit 52. The gas outlet conduit 51 has a gas outlet solenoid valve 55 disposed therein and the water outlet conduit 52 has a water outlet solenoid valve 56 disposed therein.

In the preferred embodiment, apparatus 10 includes a differential pressure transducer 60 having a high pressure port 61 and a low pressure port 62. The high pressure port 61 is in fluid communication with the water pressure sensing port 242 of the second end cap 24 of measurement vessel 20 through a pressure sensing conduit 63. The low pressure port 62 is in fluid communication with the gas pressure sensing port 233 through a gas pressure sensing conduit 64. In the preferred embodiment, a water drain solenoid valve 65 is attached to the conduit 64 for draining any water that might get entrained into the gas pressure sensing conduit. The transducer is capable of producing a voltage signal in response to a sensed differential pressure between the water pressure and gas pressure. The transducer is positioned below the measurement vessel, preferably in the range of 25 mm to 50 mm below the vessel, in order to provide a positive offset water column that will prevent a negative voltage from being generated.

Referring now to FIG. 4 which shows a frontal view of the construction of the apparatus embodying the present invention, apparatus 10 includes a programmable logic controller (PLC) 70 connected electrically to each of the water inlet, gas inlet, gas outlet, water outlet and water drain solenoid valves for sequentially operating the valves. The PLC is also electrically connected to the differential pressure transducer 60. Finally, in the preferred embodiment, apparatus 10 also includes recording means connected electrically to the differential pressure transducer 60 for collecting the voltage signal from the transducer and converting the voltage signal to an ammonia concentration value.

In the preferred embodiment, the solenoid valves are two way solenoid valves and the differential pressure transducer has a linear relationship between voltage signal and water column height. For example, if the voltage were plotted on an x-axis and the water column height were plotted on a y-axis, the linear relationship would be defined by a straight line having (x,y) coordinates of (0,0) and (5,14), the units of x being volts and the units of y being inches of water column.

In another embodiment of the present invention, a process for automated measurement of ammonia content includes providing a measurement vessel adapted for allowing height of water within the vessel to be measured and providing means for measuring the height of water within the measurement vessel. In the preferred embodiment, the means desirably include fluid head measurement means, preferably, a differential pressure transducer. The pressure transducer has a high pressure port and a low pressure port, and the pressure transducer is adapted for (i) sensing the pressure exerted by said water containing dissolved ammonia, at said high pressure port, (ii) sensing the pressure exerted by said gas mixture, at said low pressure port, and (iii) providing a voltage signal in response to a differential pressure between the respective pressures exerted by said water and said gas. The fluid head measurement means could also include an absolute pressure transducer.

In another embodiment, the means for measuring the height of water include spectrally reflective means, such as for example, an optical transmitter/laser triangulation sensor manufactured by Aromat or Keyance. Other include spectrally reflective means include an ultrasonic device, such as manufactured by Migatron, or Lundehl. Yet other devices include photoelectric devices such as those made by Banner Engineering. Other alternative means include a radio-frequency transmitter and a microwave. Such means are well known to those skilled in the art of determining fluid column height.

In another embodiment, the means for measuring the height of water include radio frequency and capacitance devices such as those made by Drexelbrook and/or mechanical float devices such as those made by Kobold.

Industrial Applicability

Referring to FIG. 1, the water is supplied to the water reservoir 30 through solenoid valve 36. Reservoir 30 is elevated above the measurement vessel to allow for gravity feed of the water into the vessel 20 during the measurement.

The following sequence is programmed into the programmable logic controller (PLC) 70 for electrically opening and closing valves 35, 45, 55, 56 and 65 in the manner as set forth in table I below.

TABLE 1

| No. | Action | Time | Duration |
|---|---|---|---|
| 1. | Open valve 56 | 0:00 | 0:15 |
| 2. | Open valve 45 | 0:05 | 0:50 |
| 3. | Close valve 56 | 0:15 | 1:40 |
| 4. | Open valve 55 | 0:15 | 0:35 |
| 5. | Close valve 55 | 0:50 | 1:35 |

TABLE 1-continued

| No. | Action | Time | Duration |
|---|---|---|---|
| 6. | Close valve 45 | 0:55 | 1:20 |
| 7. | Open valve 35 | 1:05 | 0:30 |
| 8. | Close valve 35 | 1:35 | 1:40 |
| 9. | Energize recorder | 1:35 | 0:20 |
| 10. | Open valve 45 | 1:55 | 0:15 |
| 11. | Open valve 56 | 1:55 | 0.10 |
| 12. | Close valve 56 | 2:05 | 0:05 |
| 13. | Open valve 65 | 2:05 | 0:05 |
| 14. | Close valve 45 | 2:10 | 2:05 |
| 15. | Close valve 65 | 2:10 | 0:05 |

Valve 56 is opened to drain any remaining water from vessel 20 from the previous measurement cycle. Then valve 45 is opened, valve 56 is closed and valve 55 is opened to allow the gas sample to purge vessel 20. After vessel 20 has been purged with the gas, valve 55 is closed and valve 45 is closed, thereby entrapping a fixed amount of gas. Then valve 35 is opened to allow water to drain into vessel 20. The ammonia present in the gas mixture immediately dissolves into the water and is soluble in the water. The valve 35 is timed to remain open for sufficient time to allow substantially all of the ammonia to be dissolved in the water. Valve 35 is then closed. The transducer voltage is measured. The transducer voltage is based on the sensed differential pressure between the water column and the gas blanket above the water column, the water column being measured on the high pressure side of the transducer and the gas pressure being measured on the low pressure side. After the reading has been recorded, the valve 56 is opened to drain the water from the vessel. Then valve 45 and valve 56 are opened to drive any remaining water from the vessel and thereafter valve 56 is closed. Finally, valve 65 is opened to drain any water entrained in the gas pressure sensing line and then valve 65 is closed and thereafter valve 45 is closed and the system is ready for another measurement cycle.

Other aspects, objects and advantages of this invention can be obtained from a study of the drawings, the disclosure and the appended claims.

We claim:

1. A process for automated measurement of ammonia content in a gas mixture containing water-soluble ammonia gas and one or more water-insoluble gases, comprising the steps of:

(a) providing a water reservoir adapted for (i) receiving water therein while maintaining a predetermined water level in said reservoir, and (ii) supplying water therefrom through a first solenoid valve;

(b) providing a measurement vessel adapted for (i) receiving said water from said reservoir through said first solenoid valve and draining said water from said vessel through a second solenoid valve, (ii) receiving said gas mixture at a predetermined pressure and temperature through a third solenoid valve and purging said gas mixture from said vessel through a fourth solenoid valve, (iii) maintaining said gas in said vessel and receiving said water in said vessel, said water being of sufficient amount to dissolve the ammonia gas contained in said gas mixture into said water, and (iv) allowing a differential pressure between said gas mixture and said water containing dissolved ammonia, to be measured;

(c) providing a differential pressure transducer having a high pressure port and a low pressure port, said pressure transducer being adapted for (i) sensing the pressure exerted by said water containing dissolved ammonia, at said high pressure port, (ii) sensing the pressure exerted by said gas mixture, at said low pressure port, and (iii) providing a voltage signal in response to a differential pressure between the respective pressures exerted by said water and said gas;

(d) providing a programmable logic controller connected electrically to each of (i) said first, second, third and fourth solenoid valves for sequentially operating said solenoid valves, and (ii) said pressure differential transducer; and (e) providing recording means connected electrically to said differential pressure transducer for collecting said voltage signal from said transducer and converting said voltage signal to an ammonia concentration value.

2. A process, as set forth in claim 1, including the step of (f) programming said programmable logic controller to sequentially (i) open the fourth solenoid valve, (ii) open the first solenoid valve, (iii) close the fourth solenoid valve, (iv) open the second solenoid valve, (v) close the second solenoid valve, (vi) close the first solenoid valve, (vii) open the third solenoid valve, (viii) close the third solenoid valve, (ix) energize said recording means to record measured transducer voltage and convert to an ammonia concentration value, (x) open the fourth solenoid valve, (xi) open the first solenoid valve, (xii) close the fourth solenoid valve, and (xiii) close the first solenoid valve.

3. A process, as set forth in claim 1, wherein said water is of an amount sufficient to substantially dissolve the ammonia gas into said water.

4. A process, as set forth in claim 3, wherein said water is of an amount sufficient to dissolve at least 90 mole % of the ammonia gas into said water.

5. A process, as set forth in claim 2, including the step of providing a fifth solenoid valve for draining any entrained water and preventing said entrained water from entering the low pressure port of said differential pressure transducer.

6. A process, as set forth in claim 5, including the step of providing a programmable logic controller connected electrically to said fifth solenoid valve and sequentially operating said valve by sequential steps: (xii.1) open the fifth solenoid valve, and (xii.2) close the fifth solenoid valve, immediately after said sequential step (xii) of step (f).

7. A process for automated measurement of ammonia content in a gas mixture containing water-soluble ammonia gas and one or more water-insoluble gases, comprising the steps of:

(a) providing a water reservoir adapted for (i) receiving water therein while maintaining a predetermined water level in said reservoir, and (ii) supplying water therefrom through a first solenoid valve;

(b) providing a measurement vessel adapted for (i) receiving said water from said reservoir through said first solenoid valve and draining said water from said vessel through a second solenoid valve, (ii) receiving said gas mixture at a predetermined pressure and temperature through a third solenoid valve and purging said gas mixture from said vessel through a fourth solenoid valve, (iii) maintaining said gas in said vessel and receiving said water in said vessel, said water being of sufficient amount to dissolve the ammonia gas contained in said gas mixture into said water, and (iv) allowing height of water within said vessel to be measured;

(c) providing means for measuring the height of water within said measurement vessel;

(d) providing a programmable logic controller connected electrically to each of (i) said first, second, third and fourth solenoid valves for sequentially operating said solenoid valves, and (ii) said providing means for measuring the height of water; and (e) providing recording means connected electrically to said means for measuring the height of water and for converting said measured height signal to an ammonia concentration value.

8. A process, as set forth in claim 7, wherein said means for measuring the height of water include fluid head measurement means.

9. A process, as set forth in claim 8, wherein said fluid head measurement means include a differential pressure transducer, said pressure transducer having a high pressure port and a low pressure port, said pressure transducer being adapted for (i) sensing the pressure exerted by said water containing dissolved ammonia, at said high pressure port, (ii) sensing the pressure exerted by said gas mixture, at said low pressure port, and (iii) providing a voltage signal in response to a differential pressure between the respective pressures exerted by said water and said gas.

10. A process, as set forth in claim 8, wherein said fluid head measurement means include absolute pressure measurement transducer.

11. A process, as set forth in claim 7, wherein said means for measuring the height of water include spectrally reflective means.

12. A process, as set forth in claim 11, wherein said means include an optical transmitter.

13. A process, as set forth in claim 11, wherein said means include an ultrasonic device.

14. A process, as set forth in claim 11, wherein said means include a radio-frequency transmitter.

15. A process, as set forth in claim 11, wherein said means include a microwave.

16. A process, as set forth in claim 7, wherein said means for measuring the height of water include electrical devices, said devices being one of capacitance or conductance types.

17. A process, as set forth in claim 7, wherein said means for measuring the height of water include mechanical float devices.

* * * * *